United States Patent [19]

Tomiyama

[11] Patent Number: 4,578,478

[45] Date of Patent: Mar. 25, 1986

[54] THIAZOLE DERIVATIVES AND PROCEDURE OF SYNTHESIS THEREOF

[75] Inventor: Tsuyoshi Tomiyama, Sakaki, Japan

[73] Assignee: Kotobuki Seiyaku Company Limited, Nagano, Japan

[21] Appl. No.: 553,183

[22] Filed: Nov. 18, 1983

[30] Foreign Application Priority Data

Dec. 3, 1982 [JP] Japan ................................ 57-211290

[51] Int. Cl.$^4$ ........................................... C07D 277/42
[52] U.S. Cl. ...................................... 548/193; 548/194
[58] Field of Search .............................. 548/193, 194

[56] References Cited

U.S. PATENT DOCUMENTS 4,496,571  1/1985  Yellin ................................... 514/340

FOREIGN PATENT DOCUMENTS 26674  2/1982  Japan .................................. 548/194

Primary Examiner—Robert Gerstl
Attorney, Agent, or Firm—Robert E. Burns; Emmanuel J. Lobato; Bruce L. Adams

[57] ABSTRACT

A series of new 2,4-substituted thiazole derivatives are disclosed. These compounds have anti-histaminergic activity, especially, outstanding gastric anti-secretory activity.

The compounds of this invention are obtained mainly by reacting 2-substituted-4-aminoalkyl-thiomethyl thiazole with a compound having methylthio or hydroxy group corresponding thereto.

11 Claims, No Drawings

THIAZOLE DERIVATIVES AND PROCEDURE OF SYNTHESIS THEREOF

SUMMARY OF THE INVENTION

The principal object of the present invention is to provide novel compounds having pharmaceutically effective properties.

Another object of the present invention is to provide new thiazole derivatives.

Still another object of the present invention is to provide a method of manufacturing said new thiazole derivatives.

These and other objects of the present invention will become apparent from the following description.

DETAILED DESCRIPTION OF THE INVENTION

This invention relates to a series of new thiazole derivatives and a method of manufacturing the same.

The new compounds of the present invention have the following general formula (I):

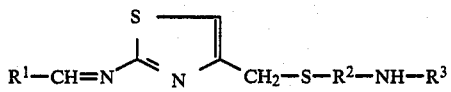 (I)

wherein $R^1$ is N,N-di-lower alkyl-amino group, $R^2$ is lower alkylene, $R^3$ is

wherein A is =N—CN or =O; B is —NH—D wherein D is lower alkyl or cyclohexyl

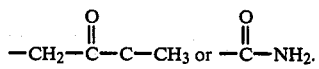

The compounds of this invention and acid addition salts thereof are therapeutically active compounds which possess anti-histaminergic activity, especially, gastric anti-secretory activity and can be administered perorally or parenterally.

To prepare the compounds of this invention, a compound of the general formula II:

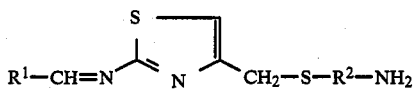 (II)

wherein $R^1$ and $R^2$ are as hereinbefore defined is reacted with a compound of the general formula III:

Y—R$^3$ (III)

wherein Y is a methylthio or hydroxy group; $R^3$ is

A and B are as hereinbefore defined.

Especially, in the general formula I, if $R^3$ is

a compound shown as the general formula I can also be obtained by reacting a compound of the general formula II with a compound of the formula:

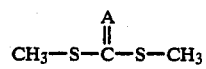

wherein A is as hereinbefore defined, and then condensing the resulting compound of the formula:

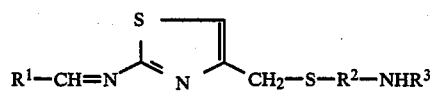

$R^1$, $R^2$ and A are as hereinbefore defined with an amine of the formula V:

H$_2$N—D (V)

wherein D is as hereinbefore defined.

The compound of the formula II is prepared by converting 2-amino-4-chloro-thiazole.hydrochloride (VI) to 2-(dialkylamino-formylamidino)-4-chloromethyl-thiazole (VII) by Vilsmeier reaction, and then it is reacted with 2-mercapto-alkylamine in the following manner:

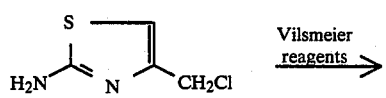

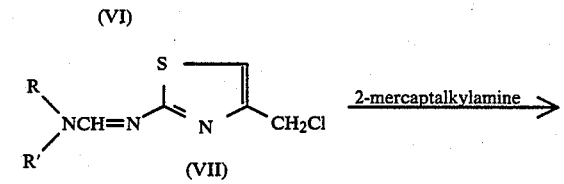

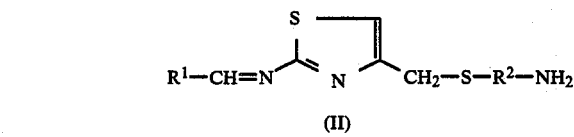

wherein R and R' are lower alkyl group

To prepare Vilsmeier reagents, N,N-di-lower alkylformamide

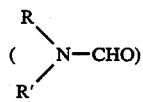

is reacted with a halogenating agent in an inert solvent such as tetrahydrofuran or dioxane under cooling conditions. As halogenating agents, phosphorus oxychloride, thionyl chloride or phosphorus trichloride are used.

The reaction of compound VII with 2-mercapto-alkylamine is performed in the presence of equimolar sodium methoxide or sodium ethoxide in alcohol under warmed conditions, if necessary.

The compounds of formula III in which Y is a methylthio group include dimethyl-N-cyanoimidothiocarbonate, N-cyano, N-alkylamidino-thiomethyl, 1,1-dicyano-2,2-dimethylthioethylene, and 1,1-dicyano-2-methylamino-2-methylthioethyl. The reaction of these compounds having a methylthio group and a compound of the general formula II is carried out at room temperature or by heating.

As in the case of reaction of dimethyl-N-cyanoimidodithiocarbonate for obtaining a compound of the general formula III having methylthio group, the reaction of an amine of the general formula V may be carried out to give the desired compound of the general formula I.

The reaction of amine of the general formula V is effected using an excessive amount of said amine alone at room temperature or by mild heating or in the presence of a silver salt such as silver nitrate.

The compounds which have the hydroxy group for symbol Y include acetyl glycolic acid and oxamic acid. In this case, the reaction of the compound III which contains a hydroxy group with compound II can be carried out with dehydrating agents such as dicyclohexylcarbodiimide, carbonyldiimidazole or diphenylphosphorylazide; or by a mixed acid anhydride method using ethylchloroformate or propylchloroformate in the presence of a base.

The purification and separation of the final products are carried out by extraction, recrystallization or column chromatography. These final products are converted to their suitable acid addition salts by a conventional methods.

The following examples will serve to illustrate the invention but do not intend to limit the scope of the invention.

REFERENCE EXAMPLE 1

2-(N,N-dimethylformyl amidino)-4-chloromethyl thiazole

To an ice-water cooled solution of 8.77 g of dimethylformamide in 35 ml of tetrahydrofuran is added 9.20 g of phosphorus oxychloride in 21 ml of tetrahydrofuran dropwise in 30 minutes. After stirring for 30 minutes at room temperature, to the reaction mixture is added 7.4 g of 2-amino-4-chloromethyl-thiazole in 28 ml of tetrahydrofuran and then stirred overnight. The reaction mixture is evaporated, 20 ml of water are added and the mixture is alkalinized with NaOH. After chloroform extraction, and washing with a saturated sodium chloride solution, the organic layer is dried by magnesium sulfate and the organic solvent is removed under reduced pressure. The residue is crystallized during its standing at room temperature and gives 8.8 g of the desired product.

M.S.(m/e): 204(M+)
ir: 3040, 1620, 1505, 1470, 1435, 1410 cm$^{-1}$

REFERENCE EXAMPLE 2

2-(N,N-diethylformylamidino)-4-chloromethyl thiazole

Following the procedure of Reference example 1, and using diethylformamide (3.03 g) instead of dimethylformamide, 2-(N,N-diethylformylamidino)-4-chloromethyl thiazole (1.83 g) can be obtained.

M.S. (m/e): 231(M+)
ir: 3060, 2960, 2850, 1660, 1600 cm$^{-1}$

REFERENCE EXAMPLE 3

2-(N,N-diethylformylamidino)-4-(2-aminoethyl)thiomethyl thiazole

To an ice-water cooled 18 ml of ethanol in which 0.54 g of metal sodium is dissolved, is added 1.35 g of cysteamine and then added N,N-diethylamidino-4-chlorothiazole during stirring. After stirring overnight, 18 ml of water is added and saturated with sodium chloride and then subjected to ethylacetate extraction. The organic phase is washed with saturated sodium chloride solution, dried and evaporated to give 1.81 g of an oily substance.

M.S. (m/e): 272(M+)
ir: 3250, 3080, 2960, 1610 cm$^{-1}$

EXAMPLE 1

N-(2-(2-(N,N-diethylformylamidino)thiazole-4-ylmethylthio)ethyl)-N'-methylamino-N"-dicyanoguanidine Step 1

N-(2-(2-(N,N-diethylformylamidino)thiazole-4-ylmethylthio)ethyl)-N'-cyano-S-methylisothio-urea.

To a solution of 1.81 g of 2-N,N-diethylformylamidino-4-(2-aminoethyl)-thiomethyl-thiazole in 18 ml ethanol is added 0.97 g of dimethyl-N-cyanoimidodithiocarbonate and stirred overnight at room temperature and the reaction mixture is evaporated under reduced pressure to give the desired product.

M.S. (m/e): 370 (M+)
ir: 3250, 2950, 2170, 1620 cm$^{-1}$
T.L.C. (ethyl acetate): Rf=0.25

Step 2

N-(2-(2-(N,N-diethylformylamidino)thiazole-4-ylmethylthio)ethyl)-N'-methylamino-N"-cyanoguanidine Material from Step 1 in an amount of 0.78 g. is dissolved in 40% methanol containing 1.9 g of methylamine and stirred overnight. The residue, after evaporation of the reaction mixture, is applied to silica gel column chromatography using ethyl acetate:ethanol (=2:1) solution as eluent to give 0.59 g of the desired oily product.

M.S. (m/e): 353 (M+)
ir: 3250, 2950, 2150, 1660 cm$^{-1}$
T.L.C. (ethanol) Rf: 0.70

EXAMPLE 2

N-(2-(2-(N,N-diethylformylamidino)thiazole-4-ylmethylthio)ethyl)-N'-propylamino-N"-cyanoguanidine To a solution of 1.0 g of material from Step 1 of Example 1 in 20 ml ethanol is added 0.6 g of silver nitrate and 4.79 g of n-propylamine and then stirred overnight. The organic phase is filtered from insoluble residue and the filtrate is evaporated. The residue is fractionated by column chromatography using 30 g of silica gel and ethyl acetate as eluent, to give 0.75 g of an oily product.

M.S. (m/e): 381 (M+)
ir: 3250, 3040, 2950, 2550, 2160, 1730, 1690, 1620 cm$^{-1}$
T.L.C. (ethyl acetate) Rf: 0.35

EXAMPLE 3

N-(2-(2-(N,N-diethylformylamidino)thiazole-4-ylmethylthio)ethyl)-N'-cyclohexyl-N"-cyanoguanidine According to the procedure of Example 2 but substituting an equivalent amount of cyclohexylamine for the n-propylamine in part, an oily product is obtained.

M.S. (m/e): 421 (M+)

ir: 3250, 2920, 2840, 2150, 1730, 1670 cm$^{-1}$
T.L.C. (ethyl acetate) Rf: 0.25

EXAMPLE 4

N-(2-(2-(N,N-dimethylformylamidino)thiazole-4-yl-methylthio)ethyl)-N'-methyl-N''-cyanoguanidine Using 2-N,N-dimethylamidino-4-(2-aminoethyl)thiomethyl thiazole obtained from the material of Reference example 1 according to the procedure of Reference example 3, a product is obtained according to the procedure of Example 1.

m.p.: 173°–175° C.

ir: 3420, 3300, 3100, 2160, 1630, 1600, 1580, 1530 cm$^{-1}$

EXAMPLE 5

N-(2-(2-(N,N-dimethylformylamidino)thiazole-4-yl-methylthio)ethyl)-oxamide

2-N,N-Dimethylformylamidino-4-(2-aminoethyl)thiomethylthiazole in an amount of 1.7 g which is obtained from the material of Reference example 1 according to the procedure of Reference example 3 and 0.6 g of oxamide is dissolved in 7 ml of dimethylformamide. To this solution is added 2.0 g of diphenylphosphoric acid in 4.5 ml of dimethylformamide under ice-water cooling conditions, then 0.7 g of triethylamine in 4.5 ml of dimethylformamide is added and the reaction mixture is allowed to stand still at room temperature overnight. After decanting the reaction mixture to ice-water, sodium chloride is added and is subjected to ethyl acetate extraction. The organic phase is washed with 2% of sodium carbonate solution and water. The residue obtained after evaporation of solvent is fractionated by silica-gel chromatography using ethanol as eluent to give 0.12 g of the desired product.

m.p.: 105°–109° C.

M.S. (m/e): 315 (M$^+$)

ir: 3300, 2900, 1640, 1540, 1460, 1400 cm$^{-1}$

EXAMPLE 6

N-(2-(2-(dimethylformylamidino)thiazole-4-yl-methylthio)ethyl)-acetyl glycolic amide To a cooled solution (0°–10° C.) of 1.2 g of acetylglycolic acid in 20 ml of tetrahydrofuran is added 1.3 g of chloroformic acid ethyl ester in 5 ml of tetrahydrofuran and then to this solution is added 1.1 g of triethylamine in 5 ml of tetrahydrofuran and stirred for 30 minutes. Then 2.5 g of 2-N,N-dimethylformylamidino-4-(2-aminoethyl)thiomethyl thiazole in 20 ml of tetrahydrofuran is added to the solution and stirred for 2–3 hours at room temperature. After extraction in the same manner as Example 5 with ethyl acetate and evaporation of the solvent, the resulting residue is fractionated by silica-gel column chromatography, using ethyl acetate as eluent to give 0.7 g of an oily product.

M.S (m/e): 345 (M$^+$+1)

ir: 3250, 3050, 2900, 1740, 1620, 1520 cm$^{-1}$

T.L.C. (ethanol) Rf: 0.55

What is claimed is:

1. A compound of the formula $$R^1-CH=N-\underset{\underset{N}{\overset{S}{\diagup\hspace{-0.3em}\diagdown}}}{C}-CH_2-S-R^2-NH-R^3$$

wherein
R$^1$ is a di-lower alkylamino group,
R$^2$ is a lower alkylene group,
R$^3$ is $$-\overset{\overset{A}{\|}}{C}-B$$

wherein
A represents =N—CN or =O and
B represents —NH—D, $$-CH_2-O-\overset{\overset{O}{\|}}{C}-CH_3 \text{ or } -\overset{\overset{O}{\|}}{C}-NH_2,$$

wherein D is a lower alkyl or cyclohexyl group, and
pharmaceutically acceptable acid addition salts thereof.

2. A compound according to claim 1 wherein A represents =N—CN.

3. A compound according to claim 1 wherein A is =O.

4. A compound according to claim 1 wherein A represents =N—CN and B is a lower alkylamino group.

5. A compound according to claim 1 wherein A represents =N—CN and B is the cyclohexylamino group.

6. A compound according to claim 1 wherein A represents =N—CN and B is $$-CH_2-O-\overset{\overset{O}{\|}}{C}-CH_3.$$

7. A compound according to claim 1 wherein A represents =N—CN and B is $$-\overset{\overset{O}{\|}}{C}-NH_2.$$

8. A compound according to claim 1 wherein A represents =O and B is the cyclohexylamino group.

9. A compound according to claim 1 wherein A represents =O and B is a lower alkylamino group.

10. A compound according to claim 1 wherein A represents =O and B is $$-CH_2-O-\overset{\overset{O}{\|}}{C}-CH_3.$$

11. A compound according to claim 1 wherein A represents =O and B is $$-\overset{\overset{O}{\|}}{C}-NH_2.$$

* * * * *